United States Patent
Sakanishi

(10) Patent No.: US 10,933,004 B2
(45) Date of Patent: Mar. 2, 2021

(54) COSMETIC COMPOSITION

(71) Applicant: DAICEL CORPORATION, Osaka (JP)

(72) Inventor: Yuichi Sakanishi, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 0 days.

(21) Appl. No.: 16/341,665

(22) PCT Filed: Oct. 3, 2017

(86) PCT No.: PCT/JP2017/035986
§ 371 (c)(1),
(2) Date: Apr. 12, 2019

(87) PCT Pub. No.: WO2018/070305
PCT Pub. Date: Apr. 19, 2018

(65) Prior Publication Data
US 2019/0365620 A1 Dec. 5, 2019

(30) Foreign Application Priority Data

Oct. 14, 2016 (JP) .............................. JP2016-202580
Nov. 7, 2016 (JP) .............................. JP2016-217223

(51) Int. Cl.
*A61K 8/42* (2006.01)
*A61K 8/86* (2006.01)
*A61Q 19/10* (2006.01)

(52) U.S. Cl.
CPC ................ *A61K 8/42* (2013.01); *A61K 8/86* (2013.01); *A61Q 19/10* (2013.01)

(58) Field of Classification Search
CPC ... A61K 8/33; A61K 8/42; A61K 8/68; A61K 8/86; A61Q 19/10
See application file for complete search history.

(56) References Cited

U.S. PATENT DOCUMENTS

| | | | |
|---|---|---|---|
| 5,665,778 | A | 9/1997 | Semeria et al. |
| 5,776,480 | A | 7/1998 | Candau et al. |
| 5,959,127 | A | 9/1999 | Semeria et al. |
| 8,313,755 | B2 | 11/2012 | Shiroyama et al. |
| 9,161,896 | B2 | 10/2015 | Yamamoto |
| 2002/0010215 | A1 | 1/2002 | Shiroyama et al. |
| 2004/0120918 | A1 | 6/2004 | Lintner et al. |
| 2006/0057091 | A1 | 3/2006 | Fujii et al. |
| 2009/0239958 | A1* | 9/2009 | Sakanishi ........... B01F 17/0028 516/9 |
| 2010/0062960 | A1 | 3/2010 | Sakanishi |
| 2017/0151159 | A1 | 6/2017 | Yamada et al. |

FOREIGN PATENT DOCUMENTS

| | | |
|---|---|---|
| CN | 103494720 B | 2/2016 |
| EP | 0 647 617 A1 | 4/1995 |
| EP | 0 720 847 A1 | 7/1996 |
| EP | 2 163 237 A2 | 3/2010 |
| JP | 8-225427 A | 9/1996 |
| JP | 2001-316217 A | 11/2001 |
| JP | 2002-338459 A | 11/2002 |
| JP | 2016-13974 A | 1/2016 |
| WO | WO 2004/045566 A1 | 6/2004 |

OTHER PUBLICATIONS

Written Opinion of the International Searching Authority dated Nov. 21, 2017, in PCT International Application No. PCT/JP2017/035986.
International Search Report dated Nov. 21, 2017, in PCT International Application No. PCT/JP2017/035986.
Extended European Search Report dated Jul. 1, 2020, in European Patent Application No. 17860783 4.

* cited by examiner

*Primary Examiner* — Sarah Pihonak
(74) *Attorney, Agent, or Firm* — Birch, Stewart, Kolasch & Birch, LLP.

(57) ABSTRACT

A transparent cosmetic composition that provides an excellent feeling in use and excellent dissolution stability of ceramide is provided.
The cosmetic composition of the present invention comprises (a) a ceramide, (b) a surfactant, and (c) water, wherein the cosmetic composition comprises (a) in an amount of 0.00001 to 5.0% by weight based on the total weight of the cosmetic composition, a polyglycerin aliphatic ether as (b) in an amount of 0.1 to 5.0% by weight based on the total weight of the cosmetic composition, and (c) in an amount of 50.0% by weight or more based on the total weight of the cosmetic composition. It is preferable that the polyglycerin aliphatic ether comprise a polyglycerin monoaliphatic ether in an amount of 75% by weight or more based on the total weight of the polyglycerin aliphatic ether and a polyglycerin dialiphatic ether in an amount of 5% by weight or less based on the total weight of the polyglycerin aliphatic ether.

3 Claims, No Drawings

COSMETIC COMPOSITION

TECHNICAL FIELD

The present invention relates to a transparent cosmetic composition that contains a specific polyglycerin aliphatic ether and in which ceramide was stably solubilized. The present application claims priority from Japanese Patent Application No. 2016-202580 filed on Oct. 14, 2016 and Japanese Patent Application No. 2016-217223 filed on Nov. 7, 2016, the contents of which are incorporated herein.

BACKGROUND ART

Ceramides are abundantly present in intercellular lipids forming a stratum corneum of epidermis, and prevent moisture evaporation by constructing a lipid barrier necessary for moisture retention and thus play an important role in maintaining the moisture of skin. Therefore, addition of ceramide to a cosmetic composition for enhancing a moisture retention effect has been studied. However, since ceramide is highly crystalline, poorly soluble in both water and oil, and prone to form a crystal at low temperature, it is very difficult to maintain ceramide in a state dissolved in the cosmetic composition stably over time and, among cosmetic compositions, particularly a toner, which contains a large quantity of water, has had the problem of decreased transparency caused by the reduction of the solubility of ceramide over time.

A known method for solubilizing ceramide stably is a method by adding a solubilizer such as a surfactant. However, this method has the following problems: the addition of the solubilizer in an amount enough to retain transparency of the toner leads to deterioration of feeling in use due to increased skin irritancy; and reduction of the solubilizer content leads to occurrence of whitishness or milkiness, precipitation, oil floating, and the like over time due to incomplete solubilization of ceramide.

Patent Literatures 1, 2, and 3 disclose a method of adding a nonionic surfactant and a polyhydric alcohol and/or a higher fatty acid as the method for solubilizing ceramide stably. However, all the methods had the problem of high skin irritancy and unfavorable feeling in use.

CITATION LIST

Patent Literature

Patent Literature 1: Japanese Patent Laid-Open No. 2002-338459
Patent Literature 2: Japanese Patent Laid-Open No. 2001-316217
Patent Literature 3: International Publication No. WO 2004/045566

SUMMARY OF INVENTION

Technical Problem

Thus, it is an object of the present invention to provide a transparent cosmetic composition that provides an excellent feeling in use and excellent dissolution stability of ceramide.

Solution to Problem

As a result of intensive research to solve the above described problems, the present inventor has found that using a specific amount of a polyglycerin aliphatic ether as a surfactant allows for solubilizing ceramide stably and obtaining a transparent cosmetic composition and that the cosmetic composition is low-irritative and has a good feeling in use. The present invention has been accomplished on the basis of these findings.

Specifically, the present invention provides a cosmetic composition comprising (a) a ceramide, (b) a surfactant, and (c) water, wherein the cosmetic composition comprises (a) in an amount of 0.00001 to 5.0% by weight based on the total weight of the cosmetic composition, a polyglycerin aliphatic ether as (b) in an amount of 0.1 to 5.0% by weight based on the total weight of the cosmetic composition, and (c) in an amount of 50.0% by weight or more based on the total weight of the cosmetic composition.

The present invention also provides the cosmetic composition, wherein the polyglycerin aliphatic ether comprises a polyglycerin monoaliphatic ether in an amount of 75% by weight or more based on the total weight of the polyglycerin aliphatic ether and comprises a polyglycerin dialiphatic ether in an amount of 5% by weight or less based on the total weight of the polyglycerin aliphatic ether.

The present invention also provides the cosmetic composition, wherein the polyglycerin monoaliphatic ether is a compound represented by the following formula (1)

wherein R represents a branched-chain aliphatic hydrocarbon group having 14 to 22 carbon atoms. n represents an average number of glycerol monomers, ranging from 2 to 15.

The present invention also provides the cosmetic composition wherein (a) the ceramide is at least one compound selected from the group consisting of (a-1) a vegetable ceramide, (a-2) a bioceramide, and (a-3) a pseudo-ceramide.

The present invention also provides the cosmetic composition wherein the content of (a) the ceramide is 0.00001 to 1.0% by weight based on the total weight of the cosmetic composition.

Advantageous Effects of Invention

The cosmetic composition of the present invention can maintain ceramide in a dissolved state stably over time, does not cause, for example, precipitation and oil floating, and has excellent transparency. Furthermore, the cosmetic composition of the present invention has an excellent feeling in use, since the polyglycerin aliphatic ether, which is low-irritative, is used as the surfactant and thus skin irritancy associated with use of the surfactant can be suppressed to a very low level. Therefore, the cosmetic composition of the present invention can be used, without particular limitations, for applications where the effect of ceramide (for example, a moisture retention effect) is required, and particularly, can be favorably used as a skin-care cosmetic such as a toner.

DESCRIPTION OF EMBODIMENTS ((a) Ceramide)
Examples of (a) a ceramide in the present invention include the following compounds. These may be used singly or in combinations of two or more.
(a-1) A vegetable ceramide (or a glycoceramide),
(a-2) A bioceramide (or a human type ceramide),
(a-3) A pseudo-ceramide (or a synthetic ceramide),
(a-4) A natural ceramide (or an animal ceramide), (a-1) The vegetable ceramide is a compound extracted from rice bran, a rice plant, a corn, *Amorphophallus konjac*, a maitake mushroom, a tamogitake mushroom, a soy bean, a beet, wheat, and the like, and has a structure in which the ceramide is linked to a sugar. The vegetable ceramide is preferably a sphingoglycolipid, particularly preferably a cerebroside, and most preferably a glucosylceramide. Specifically, the vegetable ceramide is preferably a sphingoglycolipid derived from rice bran and more preferably a glucosylceramide derived from rice bran.

(a-2) The bioceramide is a ceramide that has the same structure as a ceramide present in the horny layer of human skin and is synthesized mainly by the action of yeast. Examples of the bioceramide include ceramide 1, ceramide 2, ceramide 3, ceramide 4, ceramide 5, ceramide 6, ceramide 6II, ceramide 7, ceramide 8, ceramide 9, and ceramide 10. In the present invention, in particular, at least one selected from ceramide 1, ceramide 2, ceramide 3, ceramide 4, ceramide 5, ceramide 6, ceramide 6II, and ceramide 7 is preferable; ceramide 2, ceramide 3, ceramide 5, and ceramide 6II are more preferable; and ceramide 2 is even more preferable. Ceramide 2 is also referred to as (2S,3R)-2-octadecanoylaminooctadecane-1,3-diol.

(a-3) The pseudo-ceramide is a compound that has a ceramide-like structure and is chemically synthesized from petroleum as a raw material, and examples of the pseudo-ceramide include di(phytosteryl/2-octyldodecyl) N-lauroyl-L-glutamate, a (glycerylamidoethyl methacrylate/stearyl methacrylate) copolymer, polyquaternium 51, and N-(tetradecyloxy hydroxypropyl)-N-hydroxydecanamide.

(a-4) The natural ceramide is a ceramide that is extracted from an animal such as a horse and a pig, and examples of the natural ceramide include ceramide 1, ceramide 2, ceramide 3, ceramide 4, ceramide 5, ceramide 6, and ceramide 7.

In particular, it is preferable to use at least one compound selected from the group consisting of (a-1) the vegetable ceramide, (a-2) the bioceramide, and (a-3) the pseudo-ceramide as (a) the ceramide in the present invention, in terms of a moisture retention effect.

The content of (a) the ceramide is 0.00001 to 5.0% by weight based on the total weight of the cosmetic composition and the lower limit thereof is preferably 0.0001% by weight, particularly preferably 0.001% by weight, and most preferably 0.01% by weight. The upper limit of the content is preferably 3.0% by weight, more preferably 1.0% by weight, even more preferably 0.3% by weight, particularly preferably 0.15% by weight, and most preferably 0.10% by weight.

When the content of (a) the ceramide in the cosmetic composition is 0.00001% by weight or more, an excellent moisture retention effect is obtained. Furthermore, when the content of (a) the ceramide is 5.0% by weight or less, the ceramide can be solubilized stably over time in the cosmetic composition and thus excellent transparency is obtained. In particular, when (a-2) the bioceramide is used as (a) the ceramide, the upper limit of the content thereof is preferably 0.05% by weight. When (a-3) the pseudo-ceramide is used, the upper limit of the content thereof is preferably 0.06% by weight.

In other words, the content of (a) the ceramide is, for example, 0.00001 to 5.0 parts by weight per 100 parts by weight water contained in the cosmetic composition, and the lower limit thereof is preferably 0.0001 parts by weight, particularly preferably 0.001 parts by weight, and most preferably 0.01 parts by weight. The upper limit of (a) the ceramide content is preferably 3.0 parts by weight, more preferably 1.0 part by weight, even more preferably 0.3 parts by weight, particularly preferably 0.15 parts by weight, and most preferably 0.10 parts by weight.

When the content of (a) the ceramide is 0.00001 parts by weight or more per 100 parts by weight water contained in the cosmetic composition, an excellent moisture retention effect is obtained. Furthermore, when the content of (a) the ceramide is 5.0 parts by weight or less, the ceramide can be solubilized stably over time in the cosmetic composition and thus excellent transparency is obtained. In particular, when (a-2) the bioceramide is used as (a) the ceramide, the upper limit of the content thereof is preferably 0.05 parts by weight. When (a-3) the pseudo-ceramide is used, the upper limit of the content thereof is preferably 0.06 parts by weight.

((b) Surfactant)

(b) A surfactant in the present invention contains at least a polyglycerin aliphatic ether, which is a nonionic surfactant. Examples of the polyglycerin aliphatic ether in the present invention include a polyglycerin alkyl ether, a polyglycerin alkenyl ether, and a polyglycerin alkynyl ether.

Furthermore, it is preferable that in the polyglycerin aliphatic ether, the content of a polyglycerin monoaliphatic ether be 75% by weight or more and that the content of a corresponding polyglycerin dialiphatic ether be 5% by weight or less.

Examples of an aliphatic hydrocarbon group that forms an "aliphatic" moiety in the polyglycerin aliphatic ether (specifically, for example, the polyglycerin monoaliphatic ether and the polyglycerin dialiphatic ether) include a straight-chain or branched-chain saturated or unsaturated aliphatic hydrocarbon group. In the present invention, in particular, the branched-chain saturated or unsaturated aliphatic hydrocarbon group is preferable, and the branched-chain saturated aliphatic hydrocarbon group is particularly preferable.

The polyglycerin monoaliphatic ether is preferably a compound represented by the following formula (1):

$$RO-(C_3H_6O_2)_n-H \quad (1)$$

wherein R represents a branched-chain aliphatic hydrocarbon group having 14 to 22 carbon atoms; and n represents an average number of glycerol monomers, ranging from 2 to 15.

$C_3H_6O_2$ in the parentheses of the formula (1) has a structure represented by the following formula (2) and/or a structure represented by the following formula (3).

$$-CH_2-CHOH-CH_2O- \quad (2)$$

$$-CH_2-CH(CH_2OH)-O- \quad (3)$$

In the formula (1), R represents a branched-chain aliphatic hydrocarbon group having 14 to 22 carbon atoms. Examples of the branched-chain aliphatic hydrocarbon group may include a branched-chain saturated aliphatic hydrocarbon group such as a butyldecyl, an isomyristyl, an isocetyl, a hexyldecyl, an isostearyl, an octyldecyl, an octyldodecyl, and an isobehenyl group; and a branched-chain unsaturated aliphatic hydrocarbon group such as an isohexadecenyl, an isoheptadecenyl, and an isooleyl group. In the present invention, in particular, the branched-chain aliphatic hydrocarbon group having 14 to 20 carbon atoms is preferable, the branched-chain aliphatic hydrocarbon group having 16 to 20 carbon atoms is more preferable, and the branched-chain aliphatic hydrocarbon group having 17 to 20 carbon atoms is particularly preferable. In the present invention, among others, the branched-chain saturated aliphatic hydrocarbon group having 14 to 22 carbon atoms is preferable, the branched-chain saturated aliphatic hydrocarbon group having 14 to 20 carbon atoms is more preferable, the branched-chain saturated aliphatic hydrocarbon group having 16 to 20 carbon atoms is even more preferable, and the branched-chain saturated aliphatic hydrocarbon group having 17 to 20 carbon atoms is particularly preferable.

n represents an average number of glycerol monomers, ranging from 2 to 15. In particular, a range of 5 to 15 is preferable and a range of 8 to 12 is particularly preferable in terms of an excellent solubilization ability.

The cosmetic composition of the present invention may contain the polyglycerin monoaliphatic ether (particularly, polyglycerin mono (branched-chain saturated aliphatic) ether), wherein one polyglycerin monoaliphatic ether is used alone or two or more thereof are combined.

The content of the polyglycerin monoaliphatic ether in the polyglycerin aliphatic ether is preferably 75% by weight or more, more preferably 80% by weight or more, and particularly preferably 90% by weight or more. In this context, the upper limit of the content is 100% by weight. When the content of the polyglycerin monoaliphatic ether is 75% by weight or more, excellent water solubility is obtained. Furthermore, the amount of the polyglycerin aliphatic ether required for solubilization can be minimized, and thus, the occurrence of problems such as environmental pollution and rough skin can be suppressed to a very low level.

The content of the polyglycerin dialiphatic ether in the polyglycerin aliphatic ether is preferably 5% by weight or less, more preferably 1% by weight or less, and particularly preferably 0.5% by weight or less. In this context, the lower limit of the content is 0% by weight. When the content of the polyglycerin dialiphatic ether is 5% by weight or less, the polyglycerin aliphatic ether tends to be oriented to the interface and thus can exert an excellent solubilization ability.

Furthermore, the polyglycerin aliphatic ether may contain a polyglycerin, provided that the content of the polyglycerin is, for example, 20% by weight or less and preferably 10% by weight or less based on the total weight of the polyglycerin aliphatic ether. Furthermore, the content of the polyglycerin based on the total weight of the cosmetic composition of the present invention is, for example, 1% by weight or less and preferably 0.5% by weight or less. When the content of the polyglycerin exceeds the above described range, dispersibility in water tends to decline.

The percentage of the ingredients contained in the polyglycerin aliphatic ether (for example, the polyglycerin monoaliphatic ether and the polyglycerin dialiphatic ether) is calculated from a peak area ratio (an area ratio of a peak assigned to each ingredient relative to the total peak area), wherein the peak is detected by using a differential refractometer detector after eluting the ingredients by a column chromatographic assay such as HPLC (high speed liquid chromatography).

Examples of the above described column chromatographic assay include a reverse phase partition column-based assay that uses, as a carrier, silica gel having an octadecylsilyl group, an octylsilyl group, a butyl silyl group, a trimethyl silyl group, or a phenyl silyl group as a functional group; a normal phase partition column-based assay that uses, as a carrier, silica gel having a cyanopropyl group or an aminopropyl group as a functional group; an assay using an ion exchange column that has a quaternary ammonium group or a phenylsulfonic acid group as a functional group; and an adsorption column-based assay that uses porous silica gel. Among these assays, the reverse phase partition column-based assay that uses, as the carrier, silica gel having an octadecylsilyl group as a functional group is preferable. Furthermore, a column size is preferably 4.6 mm Φ×250 mm or more for enhancing resolution and the resolution can be further enhanced by connecting columns in series.

Examples of methods for producing the polyglycerin aliphatic ether in the present invention include the following methods:
(i) A method by addition polymerization of epichlorohydrin to an aliphatic alcohol
(ii) A method by addition polymerization of glycidol to an aliphatic alcohol
(iii) A method by reacting a polyglycerin with an aliphatic sulfate
(iv) A method by reacting an aliphatic glycidyl ether with an acetal or a ketal of glycerin and then carrying out deacetalization or deketalization.

The method (ii) described above can be used favorably in the present invention. The above described method allows for obtaining a polyglycerin aliphatic ether that contains a high percentage of the polyglycerin monoaliphatic ether. When the polyglycerin aliphatic ether thus obtained that contains a high percentage of the polyglycerin monoaliphatic ether is used, the amount thereof to be used can be suppressed to an about equal amount compared to that when the polyglycerin aliphatic ether containing 100% the polyglycerin monoaliphatic ether is used, and thus, an adverse effect (for example, rough skin) caused by excessive use of the surfactant can be suppressed.

In the method (ii), the polyglycerin aliphatic ether is obtained by converting an aliphatic alcohol represented by the following formula (4)

$$R\text{—}OH \tag{4}$$

wherein R is same as R in the formula (1) to an alkoxide by addition of an alkaline catalyst and then adding glycidol to react with the alkoxide at such a temperature that allows for sufficient stirring.

It is preferable to use, for example, a branched-chain aliphatic alcohol having 14 to 22 carbon atoms as the aliphatic alcohol represented by the formula (4), and a branched-chain saturated aliphatic alcohol having 14 to 22 carbon atoms is especially preferable. Examples of the branched-chain saturated aliphatic alcohol may include butyldecanol, isomyristyl alcohol, isocetyl alcohol, hexyldecyl alcohol, isostearyl alcohol, octyldecyl alcohol, octyldodecyl alcohol, and isobehenyl alcohol. In the present invention, in particular, the branched-chain saturated aliphatic alcohol having 14 to 20 carbon atoms is preferable, the branched-chain saturated aliphatic alcohol having 16 to 20 carbon atoms is particularly preferable, and the branched-chain saturated aliphatic alcohol having 17 to 20 carbon atoms is especially preferable. These may be used singly or in combinations of two or more.

The alkaline catalyst is preferably a compound whose catalyst residue is easy to remove after the conversion of the aliphatic alcohol to the alkoxide. Examples of the alkaline catalyst may include a basic compound resulting from replacement of some of the protons of a protic solvent by an alkaline metal cation or an alkaline earth metal cation (for example, potassium hydroxide, sodium hydroxide, lithium hydroxide, magnesium hydroxide, calcium hydroxide, sodium methoxide, sodium ethoxide, sodium butoxide, potassium methoxide, potassium ethoxide, and potassium butoxide); a basic compound resulting from replacement of some of the hydrogen atoms of a saturated hydrocarbon by an alkaline metal cation or an alkaline earth metal cation (for example, butyl lithium, methyl lithium, and ethyl lithium);

and basic metal (for example, sodium, potassium, and lithium). These may be used singly or in combinations of two or more.

The amount of the alkaline catalyst to be used is, for example, 4 to 40 mol %, and preferably 5 to 30 mol % based on the aliphatic alcohol. A catalyst concentration of lower than 4 mol % is unfavorable since self-polymerization of glycidol occurs before reaction with the alkoxide and a polyglycerin is produced as a byproduct. A catalyst concentration of higher than 40 mol % is also unfavorable since a large amount of reduced products are produced as a byproduct. It is preferable to add the alkaline catalyst before addition of glycidol. Furthermore, the alkaline catalyst may be added all at once or portionwise. Furthermore, in order to promote conversion of the aliphatic alcohol to the alkoxide after addition of the alkaline catalyst, water may be distilled while conversion to alkoxide is performed with heating or with heating under reduced pressure.

The reaction temperature for the above described addition polymerization reaction is, for example, 0 to 100° C., preferably 30 to 90° C., and more preferably 50 to 80° C. Carrying out the reaction at a temperature of 0° C. or higher enables the reaction to occur while stirring the composition in the reaction, and thus progression of the reaction can be accelerated. Furthermore, carrying out the reaction at a temperature of 100° C. or lower inhibits glycidol from self-polymerizing before reaction with the alkoxide and thus generation of a polyglycerin as a byproduct can be suppressed.

In the above described addition polymerization reaction, a low-boiling compound or an inactive solvent that does not react with glycidol (for example, acetone, ethyl acetate, butyl acetate, hexane, toluene, and xylene) may be added for the purpose of preventing increase of the reaction temperature and reducing viscosity of the crude reaction solution.

Furthermore, the addition polymerization reaction is preferably carried out under inert gas atmosphere (for example, under nitrogen gas atmosphere) in that such atmosphere can suppress hydrolysis of the alkoxide and suppress generation of a polyglycerin as a byproduct. The reaction may be carried out under pressure as necessary.

Furthermore, it is preferable to include a step of removing the alkaline catalyst after completion of the addition polymerization reaction in that a highly pure compound containing no salt derived from the alkaline catalyst can be obtained. Removal of the alkaline catalyst can be carried out for example by neutralizing the alkaline catalyst with acid and filtering off the precipitated salt.

Examples of the acid to neutralize the alkaline catalyst include an inorganic acid such as phosphoric acid, sulphuric acid, hydrochloric acid, and nitric acid; and an organic acid such as acetic acid, formic acid, butyric acid, and valeric acid. In the present invention, hydrochloric acid and phosphoric acid are especially preferable.

When the precipitated salt is filtered off, a solvent that is a poor solvent for the salt and a good solvent for the polyglycerin aliphatic ether may be added to dilute the reaction mixture and reduce viscosity thereof. Examples of the diluent solvent include alcohols, phenols, pentane, hexane, octane, benzene, acetone, ethyl acetate, and diethyl ether. These may be used singly or in combinations of two or more. In the present invention, alcohols (in particular, an alcohol having 1 to 8 carbon atoms and, among others, an alcohol having 1 to 4 carbon atoms) are especially preferable. Examples of the alcohols include a saturated aliphatic alcohol, an unsaturated aliphatic alcohol, a saturated alicyclic alcohol, and an unsaturated alicyclic alcohol, which are monohydric or polyhydric and straight-chain or branched-chain.

The amount of the diluent solvent to be added is not particularly limited to a specific amount, and it is preferable that the viscosity of the polyglycerin aliphatic ether containing a salt be reduced to such an extent that filtration can be easily carried out. For example, when the equipment for filtration is a filter press that can apply pressure at a pressure of 4 kg/cm$^2$, the viscosity of the solution is preferably 30 cps or less.

After filtration, the polyglycerin aliphatic ether is preferably subjected to a desolvation process. Regarding the condition of the desolvation process, the desolvation process may be performed at any solution temperature and at any pressure in the system and is preferably performed under inert gas airflow or under reduced pressure for preventing generation of a byproduct caused by, for example, oxidation.

The polyglycerin aliphatic ether obtained by the above described production method may be further subjected to a purification process as necessary (for example, a deodorization process by carrying out steam deodorization by blowing saturated heated steam in under reduced pressure and a decolorization process such as bleaching by sodium hypophosphite or hydrogen peroxide).

The content of the polyglycerin aliphatic ether is 0.1 to 5.0% by weight, preferably 0.4 to 4.0% by weight, particularly preferably 0.5 to 3.0% by weight, and most preferably 0.5 to 2.0% by weight based on the total weight of the cosmetic composition. When the content of the polyglycerin aliphatic ether is 0.1% by weight or more, (a) the ceramide can be solubilized in the cosmetic composition and thus a cosmetic excellent in transparency is obtained. Furthermore, the solubilized state as described above can be maintained for a long time. When the content of the polyglycerin aliphatic ether is 1.0% by weight or less, skin irritancy can be suppressed and thus a cosmetic composition that provides an excellent feeling in use is obtained.

In other words, the content of the polyglycerin aliphatic ether is 1 to 100 parts by weight, preferably 5 to 50 parts by weight, particularly preferably 10 to 30 parts by weight, and most preferably 15 to 30 parts by weight per part by weight (a) the ceramide contained in the cosmetic composition.

((C) Water)

The cosmetic composition of the present invention further contains water. The water content is 50.0% by weight or more, preferably 70.0% by weight or more, particularly preferably 80.0% by weight or more, and most preferably 90.0% by weight or more based on the total weight of the cosmetic composition. In other words, the water content is, for example, 50 to 300 parts by weight, preferably 80 to 200 parts by weight, and particularly preferably 90 to 150 parts by weight, per part by weight the polyglycerin aliphatic ether.

(Other Ingredients)

The cosmetic composition of the present invention may contain one or more kinds of other ingredients to the extent that the object of the present invention is not impaired; and the percentage of the total content of (a) the ceramide, the polyglycerin aliphatic ether, and (c) the water based on the total weight of the cosmetic composition of the present invention is, for example, 80% by weight or more, preferably 90% by weight or more, particularly preferably 95% by weight or more, and most preferably 98% by weight or more. In this context, the upper limit of the total content is 100% by weight. Therefore, the content of the other ingredients (when two or more ingredients are contained, the total content thereof) is, for example, 20% by weight or less, preferably 10% by weight or less, particularly preferably 5% by weight or less, and most preferably 2% by weight or less, based on the total weight of the cosmetic composition.

Examples of the other ingredients include a surfactant other than the polyglycerin aliphatic ether, a glycerophospholipid such as lecithin and a derivative thereof, a thickener, a wetting agent, an ultraviolet absorber, a powder, a pigment, a sugar, a high molecular compound, an ingredient for preventing rough skin, a bioactive ingredient, a transdermal absorption enhancer, an antioxidant, a pH adjustor, a chelating agent, and a perfume.

The cosmetic composition of the present invention (particularly, the toner) may also contain a polyhydric alcohol. A moist feeling is given to the cosmetic composition by containing the polyhydric alcohol. The content of the polyhydric alcohol is, for example, 5% by weight or less, preferably 3% by weight or less, and particularly preferably 1% by weight or less. When the content of the polyhydric alcohol exceeds the above described range, a micelle-forming ability thereof is impaired and dissolution stability of the ceramide tends to be reduced. Furthermore, when the content of the polyhydric alcohol exceeds the above described range, skin irritancy increases and the feeling in use tends to be worsened. Examples of the polyhydric alcohol include a polyhydric alcohol having 1 to 15 carbon atoms such as glycerol, diglycerol, maltitol, 1,3-butylene glycol, isoprene glycol, dipropylene glycol, polyethylene glycol, pentaerythritol, neopentylglycol, sorbitol, sorbitan, trehalose, and propylene glycol.

The cosmetic composition of the present invention (particularly, the toner) may also contain a higher fatty acid; and the content of the higher fatty acid is preferably 5.0% by weight or less, more preferably 1% by weight or less, and particularly preferably 0.5% by weight or less, based on the total weight of the cosmetic composition. When the content of the higher fatty acid exceeds the above described range, skin irritancy increases and the feeling in use tends to be worsened. Examples of the higher fatty acid include a long-chain fatty acid having 12 or more carbon atoms such as lauric acid, myristic acid, stearic acid, isostearic acid, and oleic acid.

The cosmetic composition of the present invention (particularly the toner) may also contain an oily ingredient (for example, a hydrogenated oil derived from animal oil or vegetable oil, a silicone-based oily phase ingredient, and a fluorine-containing oily phase ingredient); and the content of the oily ingredient is preferably 5.0% by weight or less, more preferably 1% by weight or less, and particularly preferably 0.5% by weight or less, based on the total weight of the cosmetic composition. When the content of the oily ingredient exceeds the above described range, transparency tends to decrease. In some cases, stickiness may also occur.

Adding an anionic surfactant, which has a stronger solubilization ability than the polyglycerin aliphatic ether, may be considered from the viewpoint of solubilization of (a) the ceramide, but adding the anionic surfactant to a non-rinse cosmetic is not favorable from the viewpoint of skin irritancy; and the content of the anionic surfactant is preferably 1.0% by weight or less, more preferably 0.5% by weight or less, particularly preferably 0.01% by weight or less, most preferably 0.001% by weight or less, and especially preferably 0% by weight, based on the total weight of the cosmetic composition of the present invention (particularly, the toner).

Adding ethanol, which has the effect of promoting solubilization of (a) the ceramide, to increase the ceramide content may also be considered, but the toner is often used first after washing a face and moreover used with high frequency, and thus, adding ethanol to the toner is not favorable from the viewpoint of skin irritancy. Therefore, the content of ethanol is preferably 10.0% by weight or less, more preferably 5% by weight or less, particularly preferably 1% by weight or less, most preferably 0.1% by weight or less, and especially preferably 0% by weight, based on the total weight of the cosmetic composition of the present invention (particularly, the toner).

A preservative, which is added to ensure a preservative property of the cosmetic composition, is highly irritative to skin by itself. Furthermore, among the preservatives, in particular, parabens (for example, methylparaben, ethylparaben, propylparaben, isopropylparaben, butylparaben, isobutylparaben, and benzylparaben) are poorly soluble and the amount of the surfactant needs to be increased for solubilizing these parabens; and thus the parabens are not favorable since there is a risk of further increase in skin irritancy due to the increased amount of the surfactant. Furthermore, among the preservatives, phenoxyethanol is prone to coloration over time or by temperature change. Therefore, it is preferable that the cosmetic composition of the present invention contain no preservative; and the content of the preservative is preferably 10.0% by weight or less, more preferably 5% by weight or less, particularly preferably 1% by weight or less, most preferably 0.1% by weight or less, and especially preferably 0% by weight, based on the total weight of the cosmetic composition of the present invention (particularly, the toner).

Furthermore, it is preferable that the cosmetic composition of the present invention not contain any other solubilizing ingredient if possible (for example, sterols such as cholesterol, campesterol, sitosterol, and stigmasterol; a higher alcohol such as isopalmityl alcohol, isostearyl alcohol, oleyl alcohol, Jojoba alcohol, stearyl alcohol, cetyl alcohol, and behenyl alcohol; a phospholipid such as phosphatidylcholine, phosphatidylglycerol, phosphatidylethanolamine, phosphatidylinositol, phosphatidylserine, and phosphatidic acid; a polyglycerin fatty acid ester such as decaglycerol monostearate, pentaglycerol monostearate, and decaglycerol isostearate). The content of the solubilizing ingredient (when two or more ingredients are contained, the total content thereof) is preferably 10.0% by weight or less, more preferably 5% by weight or less, particularly preferably 1% by weight or less, most preferably 0.1% by weight or less, and especially preferably 0% by weight, based on the total weight of the cosmetic composition (particularly, the toner).

The pH of the cosmetic composition of the present invention is preferably 4.5 to 8.0 in terms of an excellent ability to solubilize (a) the ceramide (or solubility).

The cosmetic composition of the present invention can be produced by, for example, a method that involves heating and mixing (a) the ceramide and the polyglycerin aliphatic ether as (b) the surfactant and then adding (c) heated water and mixing these ingredients.

The heating temperature is preferably 80° C. or more, and more preferably 85° C. or more. On the other hand, it is preferable that the heating temperature not become a too high temperature, in that oxidation or denaturation of the polyglycerin aliphatic ether and the other ingredients to be added can be suppressed; evaporation of water is suppressed when the composition contains much water, and thus the composition ratio can be maintained; and moreover, the cost and labor required for heating can be kept to a minimum. Specifically, the heating temperature is preferably 100° C. or less, and more preferably 90° C. or less. Therefore, the heating temperature is preferably 80 to 100° C., more preferably 80 to 90° C., and even more preferably 85 to 90° C.

Examples of preferable formulations of the cosmetic composition of the present invention may include formulations described below.

[1]
(a) at least one selected from the group consisting of a vegetable ceramide, a bioceramide, a pseudo-ceramide, and a natural ceramide in an amount of 0.00001 to 5.0% by weight
(b) a polyglycerin isostearyl ether and/or a polyglycerin hexyldecyl ether in an amount of 0.1 to 5.0% by weight
(c) water in an amount of 50.0% by weight or more

[2]
(a) at least one selected from the group consisting of a vegetable ceramide, a bioceramide, and a pseudo-ceramide in an amount of 0.00001 to 5.0% by weight
(b) a polyglycerin isostearyl ether in an amount of 0.1 to 5.0% by weight
(c) water in an amount of 50.0% by weight or more

[3]
(a) at least one selected from the group consisting of a vegetable ceramide, a bioceramide, and a pseudo-ceramide in an amount of 0.00001 to 5.0% by weight
(b) a polyglycerin hexyldecyl ether in an amount of 0.1 to 5.0% by weight
(c) water in an amount of 50.0% by weight or more

[4]
(a) a vegetable ceramide in an amount of 0.00001 to 5.0% by weight
(b) a polyglycerin isostearyl ether and/or a polyglycerin hexyldecyl ether in an amount of 0.1 to 5.0% by weight
(c) water in an amount of 50.0% by weight or more

[5]
(a) a bioceramide and/or a pseudo-ceramide in an amount of 0.00001 to 5.0% by weight
(b) a polyglycerin isostearyl ether and/or a polyglycerin hexyldecyl ether in an amount of 0.1 to 5.0% by weight
(c) water in an amount of 50.0% by weight or more

[6]
(a) a bioceramide and/or a pseudo-ceramide in an amount of 0.00001 to 5.0% by weight
(b) a polyglycerin isostearyl ether in an amount of 0.1 to 5.0% by weight
(c) water in an amount of 50.0% by weight or more.

The cosmetic composition of the present invention may be a cosmetic product based on the Pharmaceutical Affairs Law or a quasi drug. Examples of the cosmetic composition of the present invention include a known or conventional skin cosmetic, for example, a skin-care cosmetic such as a toner, a shaving lotion, an after-shave lotion, a cleansing lotion, and an aftersun lotion; a body-care cosmetic such as a body shampoo, a body lotion (for example, a hand care lotion and a foot care lotion), and a deodorant lotion; a hair cosmetic such as a hair shampoo, a hair rinse, a hair conditioner, a hair treatment, a hair styling liquid, a hair tonic, and a hair lotion.

The cosmetic composition of the present invention has an excellent stability over time after dissolution, and is not only transparent immediately after preparation but also free from precipitation of a crystal or cloudiness, for example, even after being allowed to stand at 25° C. for one month after preparation.

The cosmetic composition of the present invention has excellent transparency, and lightness (an L value in the L*a*b* color system) thereof immediately after preparation is, for example, 99.0 or more, more preferably 99.4 or more, particularly preferably 99.5 or more, and most preferably 99.6 or more. The cosmetic composition of the present invention can maintain transparency stably over time, and lightness thereof after being allowed to stand at 25° C. for one month after preparation is, for example, 99.0 or more, more preferably 99.4 or more, particularly preferably 99.5 or more, and most preferably 99.6 or more. In this context, lightness is one of the color attributes and represents the degree of lightness and darkness of the color. The lightness is represented by the L value (L*a*b* color system) from 0.0 to 100.0. The higher the L value is, the higher transparency is. The L value can be measured by a spectrocolorimeter.

Furthermore, the cosmetic composition of the present invention is low-irritative to skin and excellent in safety. Additionally, the inventive cosmetic composition is not sticky. Therefore, the inventive cosmetic composition provides an excellent feeling in use.

EXAMPLES

Hereinbelow, the present invention will be described more specifically by way of examples, but the present invention is not limited by the examples.
(1) Parameters for HPLC Analysis
HPLC instrument: Waters 2690 (manufactured by Waters Corporation)
Column: Wakosil 5C18 (manufactured by Wako Pure Chemical Industries, Ltd.; a reversed-phase partition column with an octadecylsilyl group as a functional group)
Developing solvent: 80% methanol and 20% $H_2O$
Flow rate: 0.5 mL/min
Column oven temperature: 40° C.
Detection method: RI
Sample concentration: 10% (solvent: 80% methanol and 20% $H_2O$)
Injection volume: 10 μL
Retention time of each ingredient is 6 minutes for a polyglycerin, 10 to 25 minutes for a polyglycerin monoaliphatic ether, and 28 to 40 minutes for a polyglycerin dialiphatic ether.
(2) Parameters for $^1$H-NMR Analysis
Analysis Instrument: 270 MHz NMR analyzer manufactured by JEOL Ltd.
Sample concentration: 1% (wt/wt)
Solvent: deuterated DMSO
Internal standard: TMS
Regarding a chemical shift of each ingredient, the chemical shift of the polyglycerin monoaliphatic ether and the polyglycerin is 2.8 ppm to 6 ppm.

Preparation Example 1 (Polyglycerin Aliphatic Ether 1)

243.45 g (1.0 mol) of hexyldecyl alcohol and 8.0 g (0.2 mol) of sodium hydroxide were placed in a four-neck flask. Next, the pressure was reduced to 10 mmHg by using an aspirator while heating to 100° C. for 90 minutes to remove moisture in the reaction system. Then, the pressure of the reaction system was returned to normal pressure, the reaction temperature was kept at 70° C. while stirring the reaction solution sufficiently under nitrogen flow, and 370.4 g (5.0 mol) of glycidol was added dropwise over 12 hours. Then, the reaction solution was neutralized to pH 7 with an aqueous phosphate solution, the pressure inside of the reaction system was reduced again while heating to distill away a low-boiling ingredient, and subsequently a salt formed by neutralization was removed by filtration to obtain a reaction solution 1.

The average number of glycerol monomers (n) of the compound contained in the obtained reaction solution 1 was about 10.1 (as determined by $^1$H-NMR analysis).

The reaction solution 1 was subjected to separation by high speed liquid chromatography and a peak area was calculated by using an infrared absorption detector. The area ratio of the polyglycerin to a polyglycerin mono(hexyldecyl) ether (the former:the latter) was 6.5:93.5; and the content of the polyglycerin mono(hexyldecyl) ether was 95.1% by weight or more and the content of a polyglycerin di(hexyldecyl) ether was 0.5% by weight or less (equal to or below the detection limit).

Preparation Example 2 (Polyglycerin Aliphatic Ether 2)

270.5g (1.0 mol) of isostearyl alcohol and 8.0 g (0.2 mol) of sodium hydroxide were placed in a four-neck flask. Next, the pressure was reduced to 10 mmHg by using an aspirator while heating to 100° C. for 90 minutes to remove moisture in the reaction system. Then, the pressure of the reaction system was returned to normal pressure, the reaction temperature was kept at 70° C. while stirring the reaction solution sufficiently under nitrogen flow, and 370.4 g (5.0 mol) of glycidol was added dropwise over 12 hours. Then, the reaction solution was neutralized to pH 7 with an aqueous phosphate solution, the pressure inside of the reaction system was reduced again while heating to distill away a low-boiling ingredient, and subsequently a salt formed by neutralization was removed by filtration to obtain a reaction solution 2.

The average number of glycerol monomers (n) of the compound contained in the obtained reaction solution 2 was about 10.3 (as determined by $^1$H-NMR analysis).

The reaction solution 2 was subjected to separation by high speed liquid chromatography and a peak area was calculated by using an infrared absorption detector. The area ratio of the polyglycerin to a polyglycerin monoisostearyl ether (the former:the latter) was 7.2:92.8; and the content of the polyglycerin monoisostearyl ether was 95.1% by weight or more and the content of a polyglycerin diisostearyl ether was 0.5% by weight or less (equal to or below the detection limit).

Examples 1 to 9 and Comparative Examples 1 to 5

Following the formulation described in the table below (unit: % by weight), first a surfactant was added to a ceramide, which had been heated to 85 to 90° C., and mixed, and water, which had been heated to 85 to 90° C., was further added and mixed, thereby obtaining a cosmetic composition. Solubility and feeling in use of the obtained cosmetic composition was evaluated by the methods described below. The results are shown together in the table below.

<Evaluation of Solubility>

For evaluation of solubility, the cosmetic compositions obtained in Examples and Comparative Examples (those immediately after preparation and those allowed to stand at 25° C. for one month after preparation) were subjected to measurement of lightness and assessment by a visual inspection and the solubility thereof was evaluated based on the following criteria.

The lightness (L value) of the cosmetic composition was measured with visible light by using a spectrocolorimeter (product name "COLOR JP7200F" manufactured by COLOR TECHNO SYSTEM CORPORATION).

Criteria of Solubility Based on the Lightness

⊙ (very good solubility): the L value is 99.5 or more

○ (good solubility): the L value is not less than 99.0 and less than 99.5

× (poor solubility): the L value is less than 99.0

The assessment by the visual inspection of the cosmetic composition was performed by checking visually the presence or absence of cloudiness, precipitation of a crystal, and oil floating on the surface of the liquid.

Criteria of Solubility Based on the Visual Inspection

○ (good solubility): none of cloudiness, precipitation of the crystal, or oil floating on the surface of the liquid is observed × (poor solubility): one or more of cloudiness, precipitation of the crystal, and oil floating on the surface of the liquid are observed <Evaluation of Feeling in Use>

Feeling in use was evaluated by performing a sensory test, in which ten panelists applied the cosmetic compositions obtained in Examples and Comparative Examples on skin and assessed feeling in use thereof (presence or absence of stickiness and skin irritancy). In this test, evaluation of feeling in use was not performed for the cosmetic compositions that had not dissolved immediately after preparation.

Criteria of Feeling in Use Based on the Sensory Test

○: neither unpleasant feeling such as stickiness or skin irritancy is sensed

×: either unpleasant feeling such as stickiness or skin irritancy is sensed

TABLE 1

Table 1

|  |  | Example 1 | Example 2 | Example 3 | Example 4 | Example 5 | Example 6 | Example 7 | Example 8 | Example 9 |
|---|---|---|---|---|---|---|---|---|---|---|
| Ceramide | A1 |  |  |  | 0.05 |  | 0.05 | 0.05 |  |  |
|  | A2 |  | 0.05 |  |  | 0.05 |  |  | 0.05 |  |
|  | A3 |  |  | 0.05 |  |  |  |  |  | 0.05 |
| Surfactant | B1 | 1 | 1 | 1 |  |  |  |  |  | 0.5 |
|  | B2 |  |  |  | 1 | 1 | 1 | 1 | 1 | 0.5 |
|  | B3 |  |  |  |  |  |  |  |  |  |
|  | B4 |  |  |  |  |  |  |  |  |  |
|  | B5 |  |  |  |  |  |  |  |  |  |
| Polyhydric alcohol | D1 |  |  |  |  |  | 1 |  | 0.5 | 0.5 |
|  | D2 |  |  |  |  |  |  | 1 | 0.5 | 0.5 |

TABLE 1-continued

Table 1

|  |  | Example 1 | Example 2 | Example 3 | Example 4 | Example 5 | Example 6 | Example 7 | Example 8 | Example 9 |
|---|---|---|---|---|---|---|---|---|---|---|
| Water | | Balance | Balance | Balance | Balance | Balance | Balance | Balance | Balance | Balance |
| Solubility (immediately after preparation) | Visual inspection | ○ | ○ | ○ | ○ | ○ | ○ | ○ | ○ | ○ |
| | L value | 99.31 | 99.42 | 99.8 | 99.78 | 99.67 | 99.86 | 99.65 | 99.79 | 99.44 |
| | Lightness | ○ | ○ | ⊙ | ⊙ | ⊙ | ⊙ | ⊙ | ⊙ | ○ |
| Solubility (25° C., after one month) | Visual inspection | ○ | ○ | ○ | ○ | ○ | ○ | ○ | ○ | ○ |
| | L value | 99.37 | 99.46 | 99.78 | 99.85 | 99.77 | 99.75 | 99.71 | 99.75 | 99.34 |
| | Lightness | ○ | ○ | ⊙ | ⊙ | ⊙ | ⊙ | ⊙ | ⊙ | ○ |
| Feeling in use | | ○ | ○ | ○ | ○ | ○ | ○ | ○ | ○ | ○ |

TABLE 2

Table 2

|  |  | Comparative Example 1 | Comparative Example 2 | Comparative Example 3 | Comparative Example 4 | Comparative Example 5 |
|---|---|---|---|---|---|---|
| Ceramide | A1 | 0.05 | 0.05 | 0.05 | | |
| | A2 | | | | 0.05 | |
| | A3 | | | | | 0.05 |
| Surfactant | B1 | | | | | |
| | B2 | | | | | |
| | B3 | 1 | | | 1 | |
| | B4 | | 1 | | | |
| | B5 | | | 1 | | 1 |
| Polyhydric alcohol | D1 | | | | | |
| | D2 | | | | | |
| Water | | Balance | Balance | Balance | Balance | Balance |
| Solubility (immediately after preparation) | Visual inspection | X | X | X | X | X |
| | L value | — | — | — | — | — |
| | Lightness | — | — | — | — | — |
| Solubility (25° C., after one month) | Visual inspection | X | X | X | X | X |
| | L value | — | — | — | — | — |
| | Lightness | — | — | — | — | — |
| Feeling in use | | — | — | — | — | — |

In the above tables, symbols A1 to A3, B1 to B5, and D1 to D2 represent the following.

A1: ceramide 2: (2S,3R)-2-octadecanoylaminooctadecane-1,3-diol), a bioceramide
A2: di(phytosteryl/2-octyldodecyl) N-lauroyl-L-glutamate, a pseudo-ceramide
A3: a sphingoglycolipid derived from rice bran, a vegetable ceramide
B1: a polyglycerin aliphatic ether 1 obtained in preparation example 1
B2: a polyglycerin aliphatic ether 2 obtained in preparation example 2
B3: polyoxyethylene hydrogenated castor oil (60E.O.)
B4: polyoxyethylene hydrogenated castor oil (40E.O.)
B5: a polyoxyethylene oleyl ether
D1: 1,3-butylene glycol
D2: dipropylene glycol To summarize the above, the constitution of the invention and variations thereof are noted below.

[1] A cosmetic composition comprising (a) a ceramide, (b) a surfactant, and (c) water, wherein the cosmetic composition comprises (a) in an amount of 0.00001 to 5.0% by weight based on the total weight of the cosmetic composition, a polyglycerin aliphatic ether as (b) in an amount of 0.1 to 5.0% by weight based on the total weight of the cosmetic composition, and (c) in an amount of 50.0% by weight or more based on the total weight of the cosmetic composition.

[2] The cosmetic composition according to [1], wherein the polyglycerin aliphatic ether comprises a polyglycerin monoaliphatic ether in an amount of 75% by weight or more (preferably 80% by weight or more, and more preferably 90% by weight or more) based on the total weight of the polyglycerin aliphatic ether and comprises a polyglycerin dialiphatic ether in an amount of 5% by weight or less (preferably 1% by weight or less, and more preferably 0.5% by weight or less) based on the total weight of the polyglycerin aliphatic ether.

[3] The cosmetic composition according to [2], wherein the polyglycerin monoaliphatic ether is a compound represented by the following formula (1):

$$RO-(C_3H_6O_2)n-H \qquad (1)$$

wherein R represents a branched-chain aliphatic hydrocarbon group having 14 to 22 carbon atoms; and n represents an average number of glycerol monomers, ranging from 2 to 15.

[4] The cosmetic composition according to [3], wherein R of the compound represented by the formula (1) is a branched-chain saturated aliphatic hydrocarbon group or a branched-chain unsaturated aliphatic hydrocarbon group.

[5] The cosmetic composition according to [4], wherein the branched-chain saturated aliphatic hydrocarbon group is a butyldecyl, isomyristyl, isocetyl, hexyldecyl, isostearyl, octyldecyl, octyldodecyl, or isobehenyl group and the branched-chain unsaturated aliphatic hydrocarbon group is an isohexadecenyl, isoheptadecenyl, or isooleyl group.

[6] The cosmetic composition according to any one of [3] to [5], wherein R of the compound represented by the formula (1) is a branched-chain aliphatic hydrocarbon group having 14 to 20 carbon atoms, preferably a branched-chain aliphatic hydrocarbon group having 16 to 20 carbon atoms, and more preferably a branched-chain aliphatic hydrocarbon group having 17 to 20 carbon atoms.

[7] The cosmetic composition according to any one of [3] to [6], wherein n of the compound represented by the formula (1) is 5 to 15 and preferably ranges from 8 to 12.

[8] The cosmetic composition according to any one of [1] to [7], wherein the content of the polyglycerin aliphatic ether is 0.4 to 4.0% by weight, preferably 0.5 to 3.0% by weight, and more preferably 0.5 to 2.0% by weight based on the total weight of the cosmetic composition, and/or is 1 to 100 parts by weight, preferably 5 to 50 parts by weight, particularly preferably 10 to 30 parts by weight, and most preferably 15 to 30 parts by weight per part by weight (a) the ceramide contained in the cosmetic composition.

[9] The cosmetic composition according to any one of [1] to [8], wherein (a) the ceramide is at least one compound selected from the group consisting of (a-1) a vegetable ceramide, (a-2) a bioceramide, (a-3) a pseudo-ceramide, and (a-4) a natural ceramide.

[10] The cosmetic composition according to any one of [1] to [9], wherein (a) the ceramide is at least one compound selected from the group consisting of (a-1) a vegetable ceramide, (a-2) a bioceramide, and (a-3) a pseudo-ceramide.

[11] The cosmetic composition according to [9] or [10], wherein (a-1) the vegetable ceramide is a glycolipid, preferably a cerebroside, and more preferably a glucosylceramide; (a-2) the bioceramide is at least one selected from ceramide 1, ceramide 2, ceramide 3, ceramide 4, ceramide 5, ceramide 6, ceramide 6II, ceramide 7, ceramide 8, ceramide 9, and ceramide 10, preferably at least one selected from ceramide 1, ceramide 2, ceramide 3, ceramide 4, ceramide 5, ceramide 6, ceramide 6II, and ceramide 7, more preferably ceramide 2, ceramide 3, ceramide 5, and/or ceramide 6II, and particularly preferably ceramide 2; (a-3) the pseudo-ceramide is at least one selected from di(phytosteryl/2-octyldodecyl) N-lauroyl-L-glutamate, a (glycerylamidoethyl methacrylate/stearyl methacrylate) copolymer, polyquaternium 51, and N-(tetradecyloxy hydroxypropyl)-N-hydroxydecanamide; and (a-4) the natural ceramide is at least one selected from ceramide 1, ceramide 2, ceramide 3, ceramide 4, ceramide 5, ceramide 6, and ceramide 7.

[12] The cosmetic composition according to any one of [1] to [11], wherein the content of (a) the ceramide is 0.00001 to 5.0% by weight based on the total weight of the cosmetic composition and the lower limit thereof is preferably 0.0001% by weight, more preferably 0.001% by weight, and particularly preferably 0.01% by weight, and the upper limit thereof is preferably 3.0% by weight, more preferably 1.0% by weight, even more preferably 0.3% by weight, particularly preferably 0.15% by weight, and most preferably 0.10% by weight.

[13] The cosmetic composition according to any one of [1] to [12], wherein the water content is 70.0% by weight or more, preferably 80.0% by weight or more, and more preferably 90.0% by weight or more based on the total weight of the cosmetic composition.

[14] The cosmetic composition according to any one of [1] to [13], wherein the percentage of the total content of (a) the ceramide, the polyglycerin aliphatic ether, and (c) the water based on the total weight of the cosmetic composition is 80% by weight or more, preferably 90% by weight or more, particularly preferably 95% by weight or more, and most preferably 98% by weight or more.

[15] The cosmetic composition according to any one of [1] to [14] that satisfies any one of the following formulations (1) to (6):

(1) (a) at least one selected from the group consisting of a vegetable ceramide, a bioceramide, a pseudo-ceramide, and a natural ceramide in an amount of 0.00001 to 5.0% by weight, (b) a polyglycerin isostearyl ether and/or a polyglycerin hexyldecyl ether in an amount of 0.1 to 5.0% by weight, and (c) water in an amount of 50.0% by weight or more (2) (a) at least one selected from the group consisting of a vegetable ceramide, a bioceramide, and a pseudo-ceramide in an amount of 0.00001 to 5.0% by weight, (b) the polyglycerin isostearyl ether in an amount of 0.1 to 5.0% by weight, and (c) water in an amount of 50.0% by weight or more (3) (a) at least one selected from the group consisting of a vegetable ceramide, a bioceramide, and a pseudo-ceramide in an amount of 0.00001 to 5.0% by weight, (b) the polyglycerin hexyldecyl ether in an amount of 0.1 to 5.0% by weight, and (c) water in an amount of 50.0% by weight or more (4) (a) the vegetable ceramide in an amount of 0.00001 to 5.0% by weight, (b) the polyglycerin isostearyl ether and/or the polyglycerin hexyldecyl ether in an amount of 0.1 to 5.0% by weight, and (c) water in an amount of 50.0% by weight or more (5) (a) the bioceramide and/or the pseudo-ceramide in an amount of 0.00001 to 5.0% by weight, (b) the polyglycerin isostearyl ether and/or the polyglycerin hexyldecyl ether in an amount of 0.1 to 5.0% by weight, and (c) water in an amount of 50.0% by weight or more (6) (a) the bioceramide and/or the pseudo-ceramide in an amount of 0.00001 to 5.0% by weight, (b) the polyglycerin isostearyl ether in an amount of 0.1 to 5.0% by weight, and (c) water in an amount of 50.0% by weight or more.

[16] The cosmetic composition according to any one of [1] to [15], wherein lightness (an L value in the L*a*b* color system) immediately after preparation is 99.0 or more, preferably 99.4 or more, more preferably 99.5 or more, and particularly preferably 99.6 or more; and/or lightness thereof after being allowed to stand at 25° C. for one month after preparation is 99.0 or more, preferably 99.4 or more, more preferably 99.5 or more, and particularly preferably 99.6 or more.

Industrial Applicability

The cosmetic composition of the present invention can maintain ceramide in a dissolved state stably over time, does not cause, for example, precipitation and oil floating, and has excellent transparency. Furthermore, the cosmetic composition of the present invention has an excellent feeling in use, since a polyglycerin aliphatic ether, which is low-irritative, is used as a surfactant and thus skin irritancy associated with use of the surfactant can be suppressed to a very low level. Therefore, the cosmetic composition of the present invention can be used, without particular limitations, for applications where the effect of ceramide (for example, a moisture retention effect) is required, and particularly, can be favorably used as a skin-care cosmetic such as a toner.

The invention claimed is:

1. A cosmetic composition comprising:
(a) a ceramide,
(b) a surfactant, and
(c) water,
wherein the cosmetic composition comprises (a) in an amount of 0.00001 to 5.0% by weight based on the total weight of the cosmetic composition, a polyglycerin aliphatic ether as (b) in an amount of 0.1 to 5.0% by weight based on the total weight of the cosmetic composition, and (c) in an amount of 50.0% by weight or more based on the total weight of the cosmetic composition,
wherein the polyglycerin aliphatic ether comprises a polyglycerin monoaliphatic ether in an amount of 75% by weight or more based on the total weight of the polyglycerin aliphatic ether and comprises a polyglycerin dialiphatic ether in an amount of 5% by weight or less based on the total weight of the polyglycerin aliphatic ether,
wherein the polyglycerin monoaliphatic ether is a compound represented by the following formula (1):

$$RO-(C_3H_6O_2)_n-H \quad (1)$$

wherein R represents a branched-chain aliphatic hydrocarbon group having 14 to 22 carbon atoms; and n represents an average number of glycerol monomers, ranging from 2 to 15,
wherein (a) the ceramide is at least one compound selected from the group consisting of (a-1) a vegetable ceramide, (a-2) a bioceramide, and (a-3) a pseudoceramide, and
wherein the cosmetic composition comprises the polyglycerin aliphatic ether in an amount of 15 to 100 parts by weight per part by weight (a) the ceramide contained in the cosmetic composition.

2. The cosmetic composition according to claim 1, wherein the content of (a) the ceramide is 0.00001 to 0.3% by weight based on the total weight of the cosmetic composition.

3. The cosmetic composition according to claim 1, wherein the water content is 90.0% by weight or more based on the total weight of the cosmetic composition.

* * * * *